United States Patent [19]

Tennican et al.

[11] Patent Number: 5,411,490
[45] Date of Patent: May 2, 1995

[54] INITIALIZATION AND ACCESS SYSTEM FOR MULTI-LUMEN CENTRAL VENOUS CATHETERS

[75] Inventors: Patrick O. Tennican; L. Myles Phipps; Russell A. Michaelsen, all of Spokane, Wash.

[73] Assignee: Hyprotek, Inc., Spokane, Wash.

[21] Appl. No.: 230,548

[22] Filed: Apr. 20, 1994

Related U.S. Application Data

[63] Continuation-in-part of Ser. No. 187,632, Jan. 26, 1994, and a continuation-in-part of Ser. No. 48,906, Apr. 19, 1993, Pat. No. 5,308,322.

[51] Int. Cl.⁶ ............................................. A61M 5/19
[52] U.S. Cl. .................................. 604/236; 604/249; 604/258; 128/762
[58] Field of Search ................. 128/762; 604/83, 187, 604/191, 124, 248, 236, 258, 249

[56] References Cited

U.S. PATENT DOCUMENTS

| | | |
|---|---|---|
| 1,948,388 | 2/1934 | Liberson . |
| 2,254,994 | 9/1941 | Butland . |
| 3,957,082 | 5/1976 | Fuson et al. . |
| 4,109,653 | 8/1978 | Kozam et al. . |
| 4,367,737 | 1/1983 | Kozam et al. . |
| 4,471,765 | 9/1984 | Strauss et al. ........................ 604/191 |
| 4,609,371 | 9/1986 | Pizzino . |
| 4,610,666 | 9/1986 | Pizzino . |
| 4,666,429 | 5/1987 | Stone . |
| 4,758,235 | 7/1988 | Tu ........................................ 604/248 |
| 4,784,157 | 11/1988 | Halls et al. . |
| 4,795,441 | 1/1989 | Bhatt .................................... 604/124 |
| 4,915,688 | 4/1990 | Bischof et al. . |
| 5,037,390 | 8/1991 | Raines et al. ......................... 604/83 |
| 5,163,554 | 11/1992 | Lampropoulos et al. . |
| 5,192,274 | 3/1993 | Bierman . |

OTHER PUBLICATIONS

"Three Easy Steps To More Convenient SASH", Block Medical, Inc., Carlsbad, Calif. 92008 (Jun. 1993).

Primary Examiner—C. Fred Rosenbaum
Assistant Examiner—Perry E. Van Over
Attorney, Agent, or Firm—Wells, St. John, Roberts, Gregory & Matkin

[57] ABSTRACT

A central venous catheter initialization and access system is disclosed for initially flushing and establishing a heparin lock in multiple lumens of a central venous catheter (CVC). The system comprises a plurality of syringes integrally mounted atop a generally planar underlying support sheet in discrete and spaced groups corresponding to individual lumens of a multi-lumen CVC. Each discrete syringe group comprises at least a flush syringe and an anti-coagulant syringe. The flush syringes are pre-filled with saline, and the anti-coagulant syringes are pre-filled with heparin. A multi-position valve assembly is also mounted atop the support sheet. The multi-position valve assembly has a plurality of individual valve inlet ports in fluid communication with the respective individual syringes, and a separate valve outlet port for each discrete syringe group. The valve outlet ports have connectors which mate with the lumens of a CVC. The valve assembly can be operated to select between the flush syringes and the anti-coagulant syringes and to provide fluid communication between the selected syringes and their corresponding outlet ports for facilitating sequential injection from the flush and anti-coagulant syringes into the individual lumens of a connected multi-lumen central venous catheter. The underlying support sheet extends beneath the components to provide a sterile underlying field during catheter access operations.

10 Claims, 8 Drawing Sheets

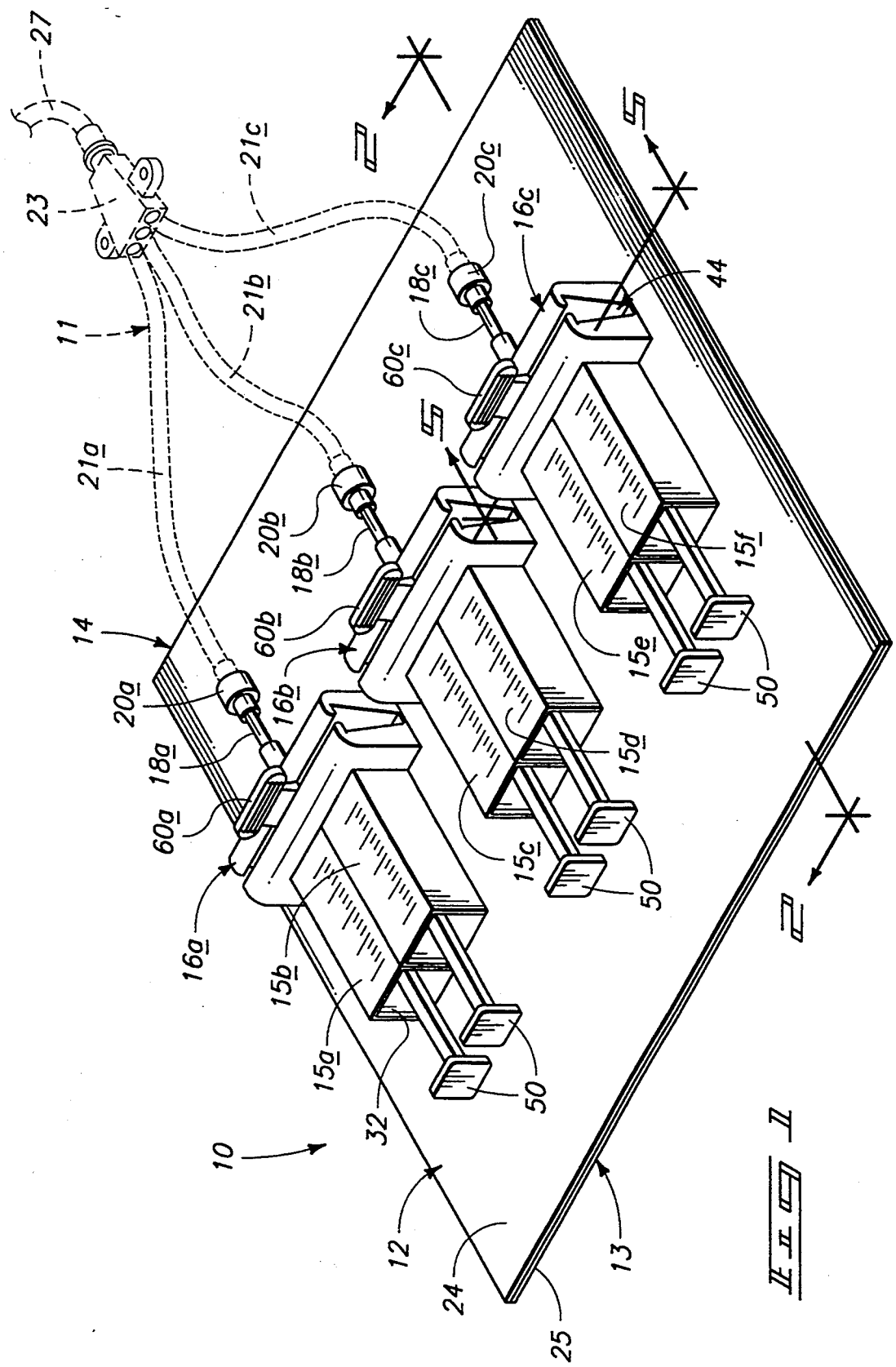

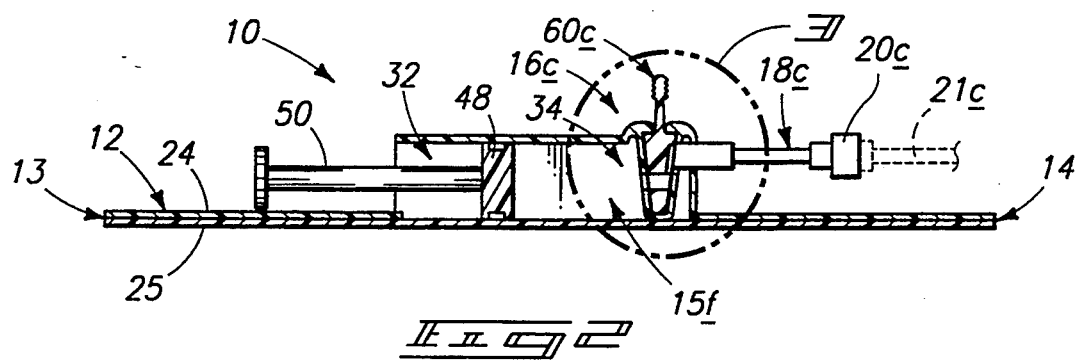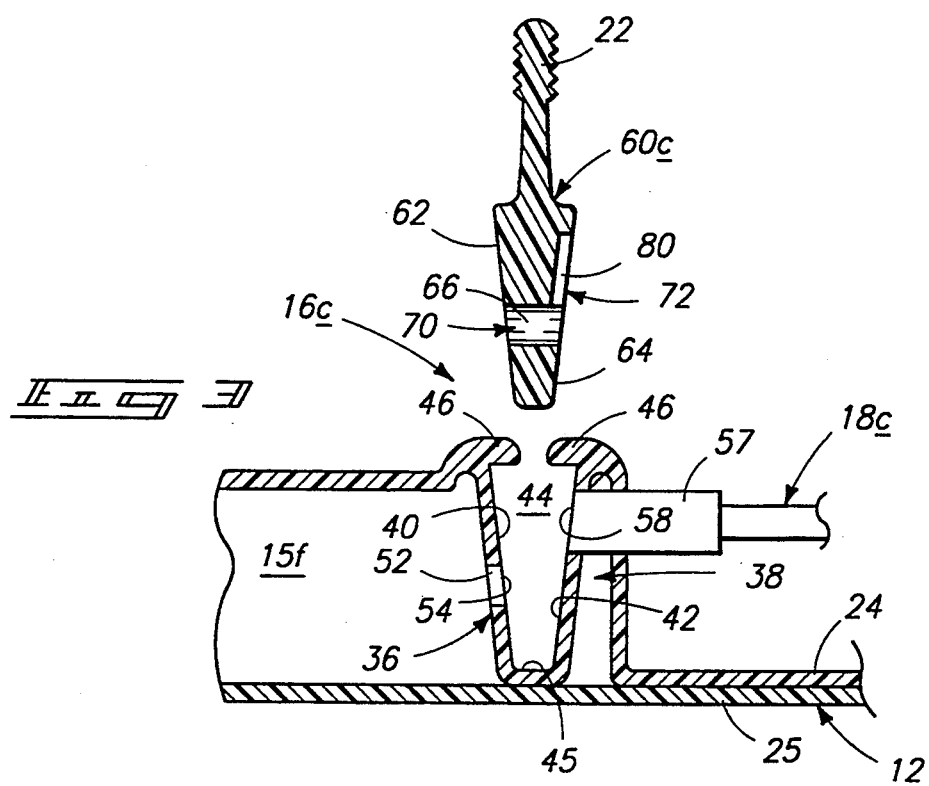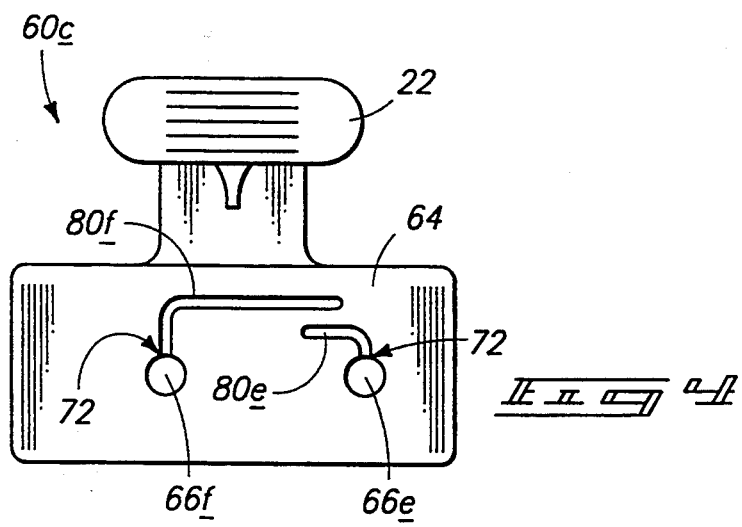

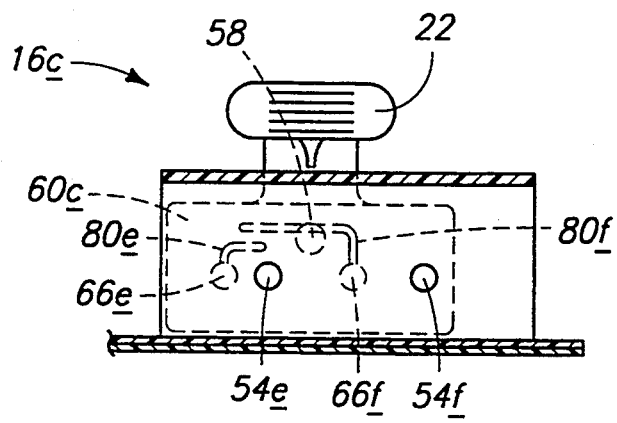
_Fig. 5_
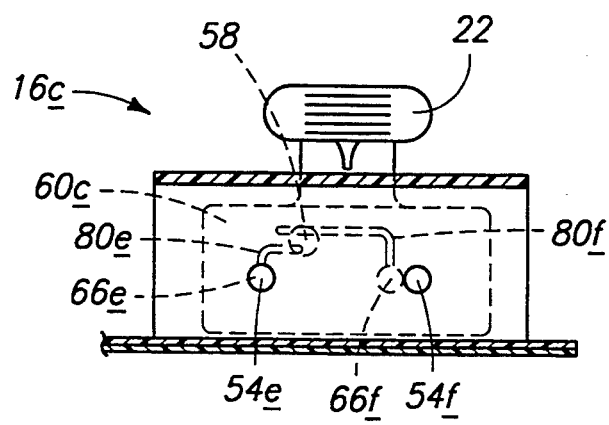
_Fig. 6_
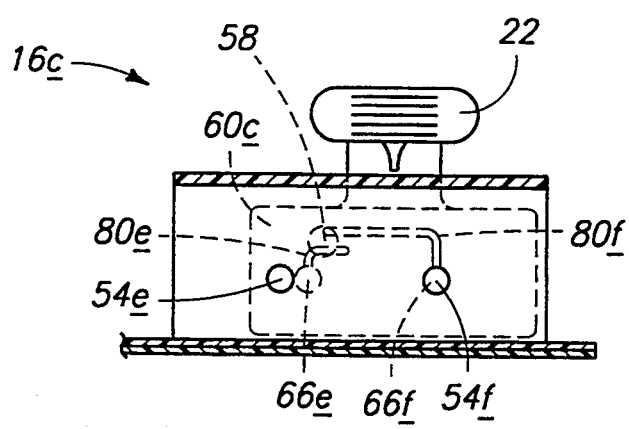
_Fig. 7_

INITIALIZATION AND ACCESS SYSTEM FOR MULTI-LUMEN CENTRAL VENOUS CATHETERS

RELATED PATENT DATA

This patent resulted from a continuation-in-part patent application of U.S. patent application Ser. No. 08/187,632, filed Jan. 26, 1994, entitled "Catheter Access System and Method," and U.S. patent application Ser. No. 08/048,906, filed Apr. 19, 1993, entitled "Central Venous Catheter Access System and Syringes," now U.S. Pat. No. 5,308,322.

TECHNICAL FIELD

This invention relates to systems for flushing and establishing heparin locks in multi-lumen central venous catheters.

BACKGROUND OF THE INVENTION

Central venous catheters (CVCs) are used in critical care situations to provide direct access to a patient's blood stream. A typical CVC includes an elongated flexible distal tube having a plurality of independent lumens extending longitudinally therethrough. Commonly used CVC's have three such internal lumens. A distal terminus of the flexible tube is adapted for placement directly in a patient's vein. The lumens open at this distal terminus. At the proximal end of the catheter, the lumens are split or Y'd into three independent flexible proximal tubes. These tubes each have an independent proximal-end injection/withdrawal port. Each such port typically includes a needle-less connector such as a Luer-lok connector. In common use, the connector is connected to a mating piece having a pierceable rubber membrane. To inject or withdraw fluid through a CVC lumen, a syringe is used, with its needle inserted into the mating piece through the rubber membrane. In some cases, syringes are connected directly to the CVC connector without a needle, thereby eliminating the need for the pierceable membrane. Each of the three catheter lumens can be independently accessed for injecting fluids into or withdrawing fluids from a patient's blood stream. An example of a CVC is shown in U.S. Pat. No. 4,894,057, which is hereby incorporated by reference.

The distal end of the CVC is inserted by a surgical procedure in a vein close to the heart. The distal tube of the catheter extends through the patient's skin. The skin entry point is sutured, dressed, and carefully monitored to avoid infections. With proper attention and care, a CVC can be left in place for relatively long times, such as days or months. Unfortunately, CVC problems are frequent, resulting in the need for frequent replacement. Most of these problems are the result of mistakes, inattentiveness, or carelessness on the part of medical personnel, and could be prevented with more careful adherence to proper procedures. While a CVC can be replaced, each such replacement requires an expensive surgical procedure and presents an unnecessary health risk to the patient.

Blood and fibrin clotting within a CVC lumen is one problem which frequently mandates CVC replacement. CVC lumens are normally kept free from clots when not in use by injecting a heparin solution into them. This is commonly referred to as a heparin lock. Heparin is a protein material which acts as a blood anti-coagulant. A heparin lock must be established in each catheter lumen immediately after CVC installation, and must be re-established after each CVC access. Failure to properly establish and maintain a heparin lock in each catheter lumen is a common cause of CVC failure and replacement.

Establishing a heparin lock is a seemingly simple procedure. Nevertheless, a lengthy sequence of steps are required, involving several different pieces of equipment. Establishing a heparin lock in a single CVC lumen, for example, requires at least the following steps. First, a nurse cleans the appropriate pierceable membrane with alcohol and/or Betadine. Next, the nurse withdraws saline into a hypodermic needle, and subsequently injects the saline into the CVC lumen, through the pierceable membrane. Finally, heparin is withdrawn into another hypodermic needle and injected into the CVC lumen.

For a triple-lumen CVC, this procedure must be repeated three times. Six different hypodermic needles and corresponding injections are needed, and there are numerous opportunities for mistakes. A mistake with any single CVC lumen can require replacement of the entire CVC.

As an additional complication, each access to a CVC by needle gives rise to a potential source of injury and infection to the care-giver through contact with the needle. This is particularly important when the patient being treated has a dangerous infection, such as HIV or hepatitis. Often, the care-giver and patient are unaware that an infection is present.

It has been observed that a surprisingly high percentage of CVC failures are the result of mistakes made during initial installation of the CVCs. This can be attributed in large part to the great number of steps required to initialize and establish heparin locks in the individual lumens of multi-lumen CVCs. Another reason for these mistakes is that the various solutions and syringes needed to perform CVC initialization are often supplied separately. A nurse must often collect these materials from different places. This can be a costly and time consuming process. Even if proper equipment is provided, it is often not designed to work together as a system.

The invention described below is a system for conveniently performing initial CVC saline flushing and anti-coagulant injection to properly establish heparin locks in each lumen of a multi-lumen CVC immediately after surgical insertion of the CVC. The invention reduces the amount of equipment which must be found and used, and greatly simplifies the entire CVC initialization process. As a result, mistakes and CVC failures are greatly reduced.

Our U.S. Pat. No. 5,308,322, formerly U.S. patent application Ser. No. 08/048,906, and U.S. patent application Ser. No. 08/187,632, are hereby incorporated by reference.

BRIEF DESCRIPTION OF THE DRAWINGS

FIG. 1 is a top perspective view of a preferred embodiment catheter initialization and maintenance system in accordance with the invention.

FIG. 2 is a sectional side view taken along line 2—2 of FIG. 1.

FIG. 3 is an enlarged and exploded sectional side view showing the circled portion of FIG. 2.

FIG. 4 is an enlarged forward end view of a sliding valve member as shown in FIGS. 1-3.

FIGS. 5–7 are enlarged diagrammatic sectional views taken along line 5—5 of FIG. 1, showing a slide valve in accordance with the invention at various sequential positions.

DETAILED DESCRIPTION OF THE PREFERRED EMBODIMENTS

Figure 8:
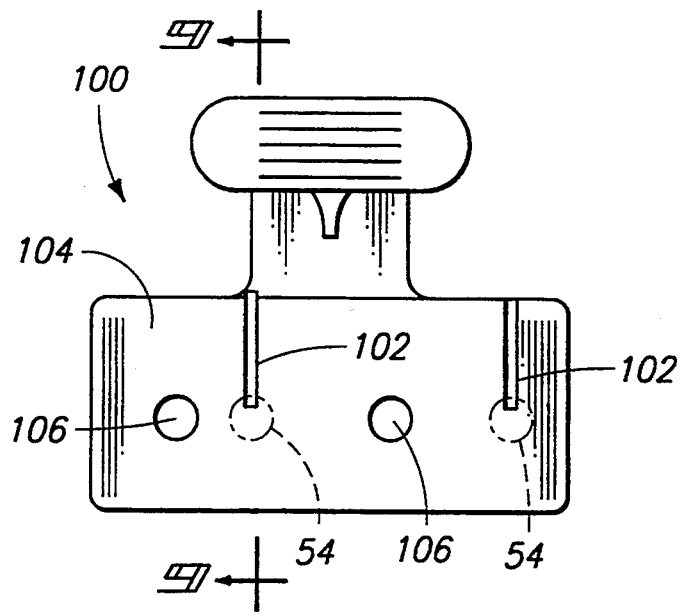
FIG. 8 is an enlarged rearward end view of an alternative sliding member in accordance with the invention.

This disclosure of the invention is submitted in furtherance of the constitutional purposes of the U.S. Patent Laws "to promote the progress of science and useful arts." U.S. Constitution, Article 1, Section 8.

In accordance with the invention, a catheter initialization and access system is disclosed for initializing and accessing a central venous catheter having multiple lumens. The disclosed system comprises:

a support base having a plurality of integrally-mounted syringes, the syringes being organized as discrete groups corresponding to individual lumens of a multi-lumen central venous catheter, each discrete group comprising at least a flush syringe and an anti-coagulant syringe;

the support base having an integrally-mounted multi-position valve assembly;

the multi-position valve assembly having a plurality of individual valve inlet ports in fluid communication with the respective individual syringes;

the multi-position valve assembly having a separate valve outlet port for each discrete group of syringes;

a plurality of mating connectors in fluid communication with the valve outlet ports for simultaneous connection of the valve outlet ports to individual lumens of a multi-lumen central venous catheter; and the valve assembly being manually actuable to selectively connect between one syringe of each discrete group and that group's corresponding valve outlet port to facilitate sequential injection from the flush and anti-coagulant syringes into individual lumens of a multi-lumen central venous catheter.

FIGS. 1–4 show a catheter initialization, maintenance, and access system in accordance with a preferred embodiment of the invention, indicated generally by reference numeral 10. Catheter initialization system 10 is for connection to and use with a multi-lumen central venous catheter (CVC) such as indicated in FIG. 1 by reference numeral 11. CVC 11 includes a plurality of individual flexible tubes or lumens 21a–21c, each of which terminates in an individual Luer-lok connector. Lumens 21a–21c converge at a hub 23, and continue independently through a single distal-end flexible tube 27 as described above.

Catheter initialization system 10 includes a rectangular and generally planar underlying sterile support sheet or base 12. Support base 12 extends in a longitudinal direction from a rearward end 13 to a forward end 14. Initialization system 10 also includes a plurality of syringes or syringe barrels 15a–15f (referred to collectively as syringes 15) and a plurality of multi-position syringe selection slide valves 16a–16c, all of which are integrally mounted to and atop support base 12. Slide valves 16a–16c collectively form a valve assembly, referred to herein as valve assembly 16. Valve assembly 16 is positioned toward forward end 14 of support base 12 forwardly from syringes 15.

The individual syringes are organized and grouped as three discrete groups of two. Each distinctly grouped pair is laterally spaced from each of the other syringe groups. Each group corresponds to an individual lumen of CVC 11. One syringe of each group is designated as a flush syringe and the other syringe of each group is designated as an anti-coagulant syringe. For instance, individual syringes 15a and 15b comprise a first syringe group corresponding to a first CVC lumen 21a. Syringe 15a is a flush syringe and syringe 15b is an anti-coagulant syringe. Individual syringes 15c and 15d comprise a second syringe group corresponding to a second CVC lumen 21b. Syringe 15c is a flush syringe and syringe 15d is an anti-coagulant syringe. Individual syringes 15e and 15f comprise a third syringe group corresponding to a third CVC lumen 21c. Syringe 15e is a flush syringe and syringe 15f is an anti-coagulant syringe. The flush syringes are preferably pre-filled with a flush solution such as saline, and the anti-coagulant syringes are preferably pre-filled with an anti-coagulant solution such as heparin.

Valve assembly 16 has a plurality of individual inlet ports in fluid communication with the respective individual syringes 15a–15f. It also has a valve outlet port corresponding to each syringe group, for connection to one of the lumens of a multi-lumen CVC. The valve assembly is manually actuable to selectively connect between one syringe of each group and that group's corresponding valve outlet port. Thus, each syringe group can be individually and simultaneously connected to a different CVC lumen to facilitate sequential injection from the flush and anti-coagulant syringes into the individual lumens of a multi-lumen CVC.

More specifically, a separate one of slide valves 16a–6c is associated with each syringe group and with each CVC lumen. Slide valve outlet tubes or ports 18a–18c extend from slide valves 16a–16c, respectively, toward base forward end 14. Individual mating connectors 20a–20c are positioned at the outer ends of outlet tubes 18a–18c, in fluid communication therewith, for simultaneous connection of valve outlet ports 18a–18c to individual CVC lumens 21a–21c. Connectors 20 are preferably needle-less connectors such as threaded Luer-lok connectors.

Slide valve assembly 16 has at least one valve member which is movable by a handle or knob 22 to select between the flush syringes and the anti-coagulant syringes, and to provide fluid communication between the selected syringes and their corresponding outlet ports. Said valve member, move specifically, is movable to selectively and exclusively connect at least one of the flush syringes or at least one of the anti-coagulant syringes to its corresponding outlet port. For instance in the preferred embodiment, each slide valve 16 has a flush position which connects the flush syringe of the associated syringe group to its respective outlet port. Each slide valve 16 likewise has an anti-coagulant position which connects the anti-coagulant syringe of the associated group to its respective outlet port.

The specific construction of system 10 is described more fully below with reference to FIGS. 2-4, which show components associated with individual slide valve 60c. It should be understood that slide valves 60a and 60b are formed in an identical manner, although they are not specifically described in the following discussion. Support base 12 is formed by laminated first and second (upper and lower) base sheets 24 and 25. Upper base sheet 24 is integrally molded to form a plurality of generally rectangular syringe channels in a thin sheet of medically-approved plastic such as high-density polypropylene, using common blow-molding or injection processes. The syringe channels project upwardly or outwardly from upper sheet 24, having rectangular transverse cross sections and longitudinal lengths which are formed along upper sheet 24. The channels are open toward the bottom or under side of upper sheet 24. They extend from rearward ends 32 to forward ends 34. After molding, rearward ends 32 are opened by cutting them away for plunger insertion. Forward ends 34 remain closed, but for fluid passages which are described below.

Upper base sheet 24 is further molded to form first and second opposed and elongated slide valve walls 36 and 38 corresponding to each of slide valves 16a-16c. This is best illustrated in FIGS. 2 and 3. Slide valve walls 36 and 38 are upstanding ridges molded in upper sheet 24 to project and extend upwardly therefrom. They are open toward the bottom of upper sheet 24. The channels which form the associated syringes intersect first slide valve wall 36. The opposed slide valve walls define and form first and second inner wall or valley surfaces 40 and 42 which in turn form a longitudinal and upwardly-open synclinal valley 44 therebetween. Base sheet 24 forms a flat valley floor 45 between valley walls 36 and 38. Retaining lips 46 are formed along the tops of the slide valve walls.

Lower base sheet 25 is preferably a planar sheet of plastic, such as medically-approved high-density polypropylene. Initialization system 10 is formed by laminating planar lower sheet 25 beneath upper sheet 24. This closes the syringe channels formed by upper sheet 24 to form syringes 15. An independently operable syringe plunger 48 (FIG. 2) is slidably received within each syringe channel. Each syringe plunger 48 is preferably rectangular to fit snugly and sealingly within its syringe barrel. An elongated handle 50 extends from each plunger 48, through open rearward end 32 of the corresponding syringe.

A plurality of apertures 52, formed through first valley wall 36, form both syringe outlet apertures and slide valve inlet ports. They are referred to in the following discussion as slide valve inlet ports. A slide valve inlet port 52 corresponds to each syringe 15 associated with the slide valve. Thus, in the preferred embodiment the first valley wall of slide valve 16c has two valve inlet ports, corresponding to flush and anti-coagulant syringes 15e and 15f. The valve inlet ports extends from the interior of the associated syringe, through first valley wall 36, and into valley 44. The inlet ports form corresponding inlet port orifices 54 in first valley surface 40. Slide valve outlet port 18c includes an enlarged terminating conduit 57 which extends through second valley wall 38 and into valley 44, forming a single outlet port orifice 58 in second wall surface 42.

While syringes 15 are integrally formed with support base 12 in the preferred embodiment, an initialization system in accordance with the invention could also use non-integrally formed syringes such as conventional cylindrical plastic syringes. Such syringes would be connected with their outlet apertures in fluid communication with slide valve inlet ports 52, possibly with mating Luer-lok connectors.

The preferred embodiment shown in FIGS. 1-4 includes a separate movable valve member associated with each slide valve 16. Each movable valve member in the preferred embodiment is an elongated sliding member such as referenced in FIGS. 1-4 by reference numerals 60a-60c. As illustrated in FIG. 3, sliding member 60c is received within slide valve 16c for linear sliding movement along a longitudinal axis within valley 44. Sliding member 60c is movable between a plurality of discrete longitudinal positions to individually select one of the associated slide valve inlet ports 52 for connection to slide valve outlet port 18c. It is retained in valley 44 by retaining lips 46. Handle 22 protrudes upwardly from between retaining lips 46.

Sliding member 60c is preferably a wedge-shaped solid body which is complementary in shape to synclinal valley 44 so that it fits tightly therein while still being capable of longitudinal sliding motion. It can be inexpensively mass-produced by injection molding a medically-approved plastic. Member 60c has first and second opposed sliding surfaces 62 and 64 which are in sliding abutment with surfaces 40 and 42, respectively, of valley walls 36 and 38; and with inlet and outlet orifices 54 and 58, respectively.

Sliding member 60c has a plurality of sliding member passageways 66 formed therethrough from first sliding surface 62 to second sliding surface 64. One passageway 66 corresponds to each associated inlet port 52 and to each associated syringe 15. The passageways are labelled in FIG. 4 with suffices e and f to indicate their correspondence with either flush syringe 15e or anti-coagulant syringe 15f. Sliding member 60a likewise has passageways corresponding to syringes 15a' and 15b. Sliding member 60b has passageways corresponding to syringes 15c and 15d. The passageways are located so that a different passageway 66 connects between a corresponding slide valve inlet port 52 and slide valve outlet port 18 at different longitudinal positions of sliding member 60c.

More specifically, each passageway 66 has a first open termination 70 (FIG. 3) along first sliding surface 62 for selective communication with a corresponding inlet port 52. Each passageway 66 also has a second open termination 72 along second sliding surface 64 to communicate with outlet orifice 58.

First open terminations 70 are simply the circular openings of passageways 66 along first sliding surface 62. First open terminations 70 are positioned so that a single one of first open terminations 70 is aligned with a corresponding one of inlet port orifices 54 at a corresponding one of the discrete longitudinal positions of sliding member 60. Said single one of first open terminations 70 is sealed by first valley surface 40 at other discrete longitudinal positions of sliding member 60.

Such selective alignment is accomplished in the preferred embodiment by spacing inlet port orifices 54 longitudinally from each other along first valley surface 40 at a first regular pitch or spacing. Passageways 66 and first open terminations 70 are spaced longitudinally from each other along first sliding surface 62 of sliding member 60 at a second regular pitch or spacing. The first and second regular pitches are different from each other, so that no more than a single one of first open terminations 70 is aligned with an inlet port orifice 54 at any single discrete longitudinal position of elongated sliding member 60. The first pitch is greater than the second pitch in the preferred embodiment.

Second open terminations 72 preferably comprise elongated open channels 80 formed in and along second sliding surface 64 of sliding member 60. The open channels are positioned against second valley surface 42, so that valley wall 38 seals against the channels. Each of the second open terminations is positioned to align with outlet port orifice 58 at least one of the discrete longitudinal positions of elongated sliding member 60. More specifically, the channel associated with each passageway 66 is positioned so that it aligns with outlet port orifice 58 when the passageway's first open termination 70 is aligned with its corresponding inlet port orifice 54. This particular arrangement of passageways and channels defines an exclusive course for fluid communication between the selected slide valve inlet port and the slide valve outlet port to restrict mixing of fluids from different syringes. When an individual syringe is selected by properly positioning sliding member 60c, there is only a single course for fluid from the selected syringe to outlet port 18c. This course does not cross the course used by the fluid of any other syringe when it is selected. While more than one of channels 80 may be aligned with outlet port aperture 58 at any single sliding member position, fluid flow into or through non-selected passageways is prevented by the sealing of first valley surface 40 against those passageways' first open terminations 70.

FIGS. 5-7 illustrate the selective and sequential alignment of inlet port orifices 54 and passageways 66 resulting from positioning sliding member 60c. The various orifices, ports, and passageways are indicated by reference numeral suffixes "e" and "f", corresponding to syringes 15e-15f, respectively.

In FIG. 5, sliding member 60c is shown in an initial "0", "off", or sealed position, in which none of inlet port orifices 54 are aligned with any of the sliding member passageways 66. Each of slide valve inlet ports 52 is sealed off at its orifice 54 by the abutting first sliding surface 62 of sliding member 60.

FIG. 6 shows a first or "1" position of sliding member 60 in which a first, single inlet port orifice 54e aligns with a first, single corresponding sliding member passageway 66e. In this position, a first channel 80e, associated with first passageway 66e, is aligned for fluid communication with outlet port orifice 58. Moving sliding member 60 to this first position therefore establishes fluid communication from syringe 15e to outlet port 18c.

FIG. 7 shows a second or "2" position in which a second, single inlet port orifice 54f aligns with a second, single corresponding sliding member passageway 66f. In this position, a second channel 80f, associated with second passageway 66f, is aligned for fluid communication with outlet port orifice 58. Moving sliding member 60 to this second position therefore establishes fluid communication from syringe 15f to outlet port 18c.

The construction and fabrication methods described above should be inexpensive to implement. Most of the components are formed by upper sheet 24. For instance, the syringes, the slide valve walls, and internal individual fluid passages are formed by the upper sheet. This formation, in addition to being inexpensive, provides a planar base which can be conveniently taped to a patient or clipped to a patient's gown during catheter access operations. Furthermore, the planar support base extends beneath mating connectors 20. When the initialization system is packaged in a sterile condition, base 12 provides a sterile field underlying the access components, facilitating sterile connection procedures. Taping the base to a patient greatly simplifies the task of maintaining the cleanliness and sterility of components during catheter access.

In use, the syringes are pre-filled with saline and heparin. The base is appropriately held or secured to the patient, and Luer-lok connectors 20 are connected to the individual lumens of a newly-installed central venous catheter. Slide valve 16a is then positioned in its flush position, and associated flush syringe 15a is operated to inject saline through CVC lumen 21a. Slide valve 16a is then positioned in its anti-coagulant position, and associated anti-coagulant syringe 15b is operated to inject a proper amount of heparin into CVC lumen 21b. This procedure is repeated for each of the slide valves and associated CVC lumens, to separately flush and establish heparin locks in each of the lumens.

Appropriate indicia are provided on or adjacent slide valve assembly 16 to indicate proper handle positions and to prompt the care-giver to carry out the administration steps in the correct sequence. Valve positions are preferably arranged so that sliding each handle 22 in one direction, to sequential positions, will facilitate the desired order of steps. The positioning and spacing of the syringe groups, in immediate proximity to the associated slide valves, provides further visual indication to the care-giver of the appropriate operation of the syringes and valves.

In a slight variation of the embodiment described above, not shown, each outlet port 18 is fastened directly to the sliding member of the associated slide valve rather than to second valley wall 38. A slot is provided in second valley wall 38 to accommodate outlet tube 18 and to provide for movement of outlet tube 18 with sliding member 60. Sliding member 60 is provided with internal passageways similar to passageways 66 described above. However, rather than having open channels, the passageways is formed within sliding member 60 to converge at outlet port 18 from their first open terminations.

Figure 9:
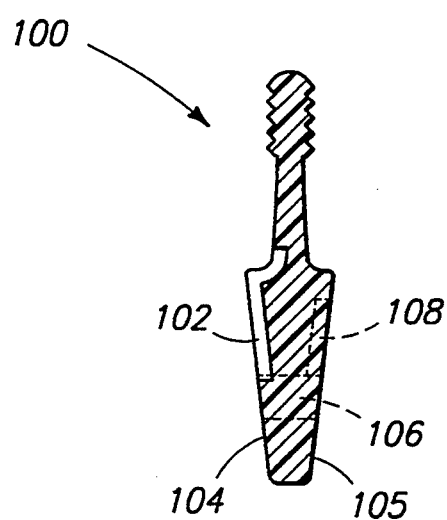
FIG. 9 is a sectional side view taken along line 9—9 of FIG. 10.

FIGS. 8 and 9 illustrate an additional slide valve feature which could advantageously be incorporated in the initialization system described above. FIGS. 8 and 9 show an alternatively constructed sliding member 100 which is largely identical to sliding member 60 described above. Sliding member 100 has internal passageways 106, similar to passageways 66 described above, first and second sliding surfaces 104 and 105, and passageway channels 108 on second sliding surface 105. However, sliding member 100 has additional vent passageways for venting connected syringes prior to fluid administration. More specifically, sliding member 100 has two vent channels 102 formed vertically along its first sliding surface 104. Vent channels 102 are positioned to simultaneously align with all of the associated inlet port orifices 54 at a single position of sliding member 100, and to extend upward therefrom to a point above first valley wall 36. Inlet port orifices 54 are shown in dashed lines in FIG. 8 to indicate this alignment. Vent channels 102 define a sliding member syringe vent position, preferably between the "0" and "1" positions described above. With sliding member 100 in the vent position, the vents simultaneously connect from all the slide valve inlet ports to ambient atmosphere, thus allowing air to be expelled from connected syringes prior to actual CVC injections.

Figure 10:
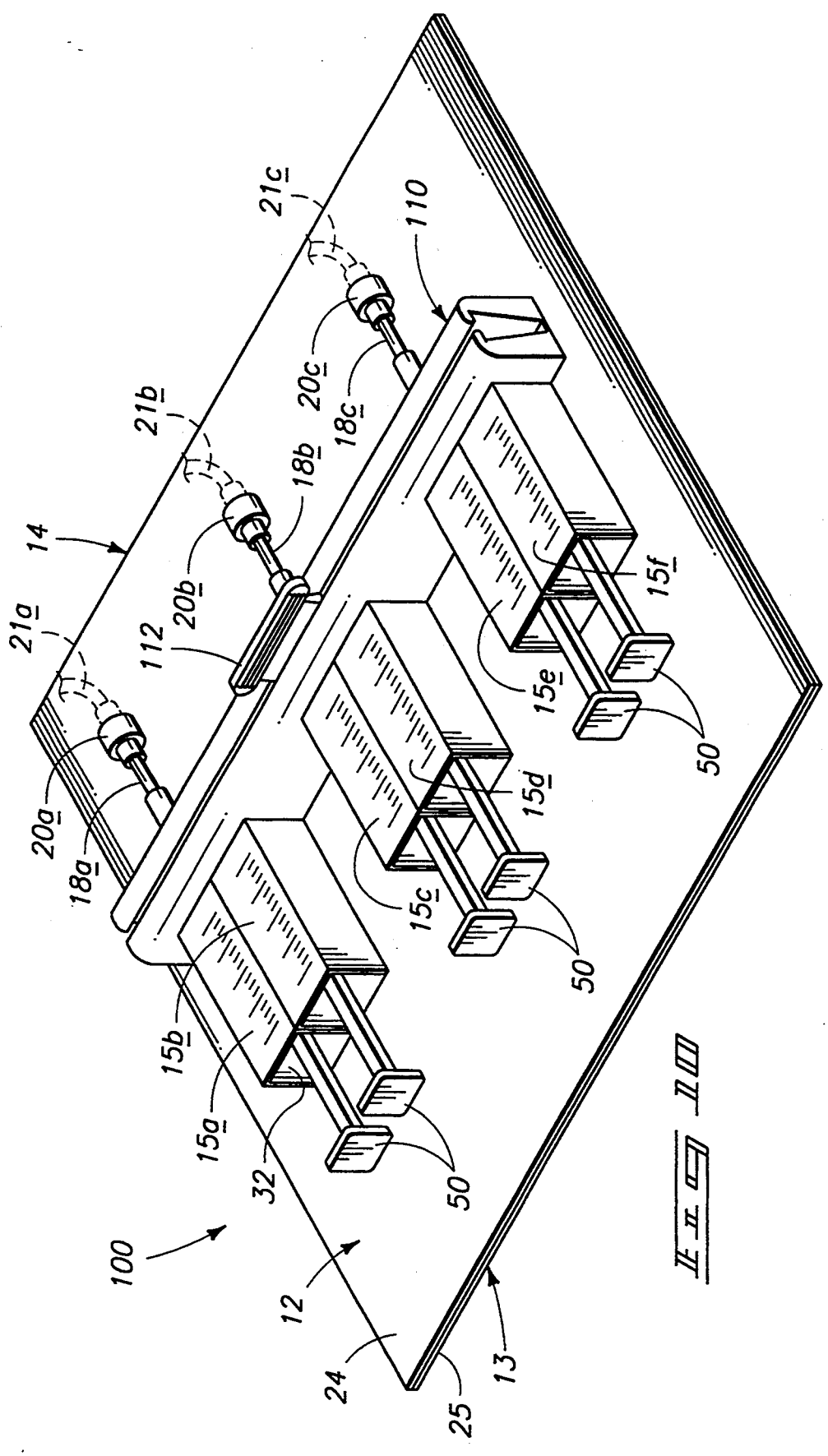
FIG. 10 is a top perspective view of an alternative embodiment catheter initialization and maintenance system in accordance with the invention.
Figure 11:
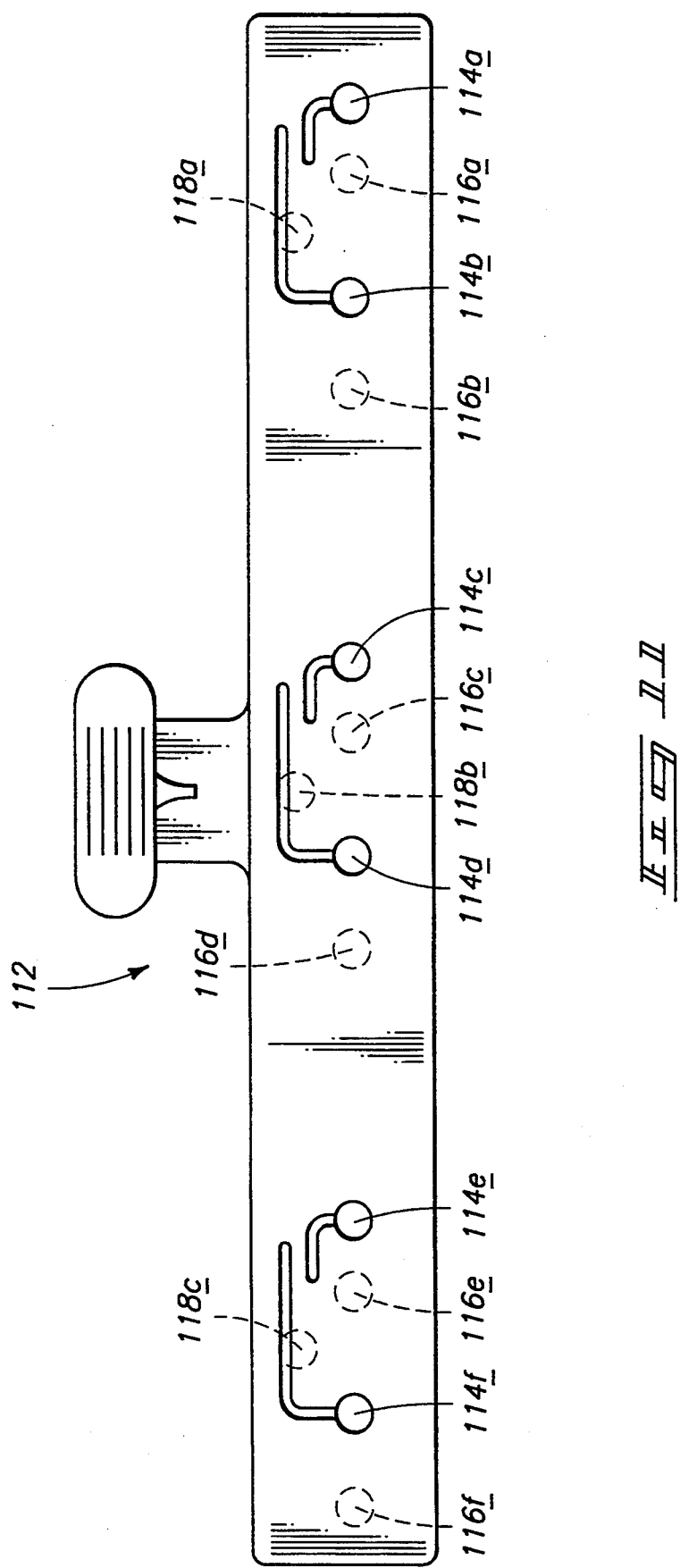
FIG. 11 is an enlarged forward end view of a sliding valve member as shown in FIG. 10.

FIGS. 10 and 11 illustrate an alternative embodiment CVC initialization system, referenced by numeral 100. System 100 is, for the most part, identical to system 10 described above. The same reference numerals are therefore used to designate identical components. System 100 differs from system 10 in that its valve assembly has only a single slide valve 110, and a single movable valve member 112. Single valve member 112 has three sets of passageways 114 (FIG. 11) which are similar to passageways 66 of FIGS. 3 and 4. Slide valve 110 has valve inlet ports 116a–116f and valve outlet ports 118a–118c (shown by dashed lines in FIG. 11) positioned and spaced just like those described above. Single valve member 112 is manually movable between a flush position and an anti-coagulant position. The passageways of single valve member 112 are aligned so that they simultaneously connect all of the individual flush syringes to their respective outlet ports when valve member 112 is in its flush position. The passageways connect all of the individual anti-coagulant syringes to their respective outlet ports when valve member 112 is in its anti-coagulant position. In operation, a care-giver would first move valve member 112 to its flush position and operate all of the flush syringes. The care-giver would then move valve member 112 to its anti-coagulant position and operate all of the anti-coagulant syringes.

It may, alternatively, be desirable provide for six positions of valve member 112. With this configuration, passageways 114 are arranged so that only a single one of syringes 15a–15f is connected to its respective outlet port at any single position of valve member 112. A care-giver would move the valve member to its first position and inject saline into a first CVC lumen, move the valve member to its second position and inject heparin into the first CVC lumen, and so on for each CVC lumen.

Figure 12:
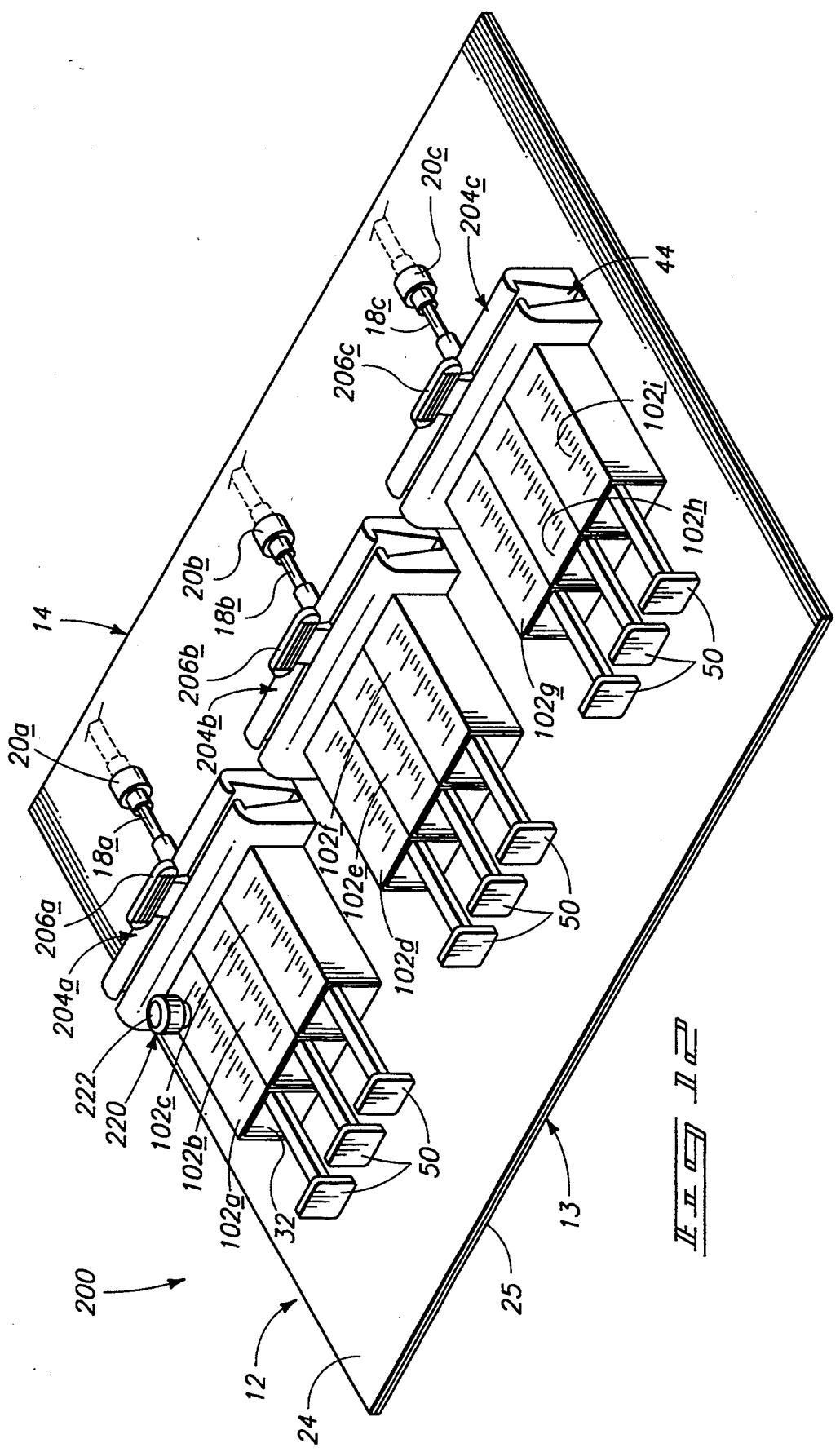
FIG. 12 is a top perspective view of an alternative embodiment catheter initialization and maintenance system in accordance with the invention.

FIG. 12 shows an alternative embodiment catheter initialization and access system 200. System 200 is constructed in accordance with the description set forth above except as noted. Components of system 200 which are the same as described in the embodiment described above with reference to FIGS. 1–4 are referenced by the same reference numerals, and are not described again in detail. System 200 differs primarily in that each discrete syringe group comprises three syringes rather than two. Each group includes pre-filled saline and anticoagulant syringes, as described above, and additionally includes a fluid withdrawal syringe. For instance, a first syringe group includes a fluid withdrawal syringe 102a, a saline injection syringe 102b, and an anticoagulant injection syringe 102c. The second and third syringe groups are similarly arranged. The fluid withdrawal syringe is initially empty. It is used to withdraw blood through a catheter lumen prior to saline injection. This is referred to as obtaining a blood return and is often necessary during initialization of some types of multi-lumen catheters in order to evacuate air from their lumens.

System 200 includes a slide valve assembly 204 which is similar to slide valve assembly 16 already described, except that is has positions corresponding to each of the three types of syringes. Valve assembly 204 is manually actuable to connect between one syringe of each discrete group and that group's corresponding valve outlet port 18 to facilitate sequential connection of the fluid withdrawal syringe, the saline syringe, and the anticoagulant syringe to the corresponding outlet port 18.

In the embodiment shown by FIG. 12, valve assembly 204 comprises three separate sliding valve members 206. Each valve member is movable between a fluid withdrawal position, a saline injection position, and an anti-coagulant injection position. In the fluid withdrawal position, the corresponding fluid withdrawal syringe is selected and connected to the corresponding outlet port. In the saline injection position, the corresponding saline syringe is selected and connected to the corresponding outlet port. In the anti-coagulant injection position, the corresponding anti-coagulant syringe is selected and connected to the corresponding outlet port.

Figure 13:
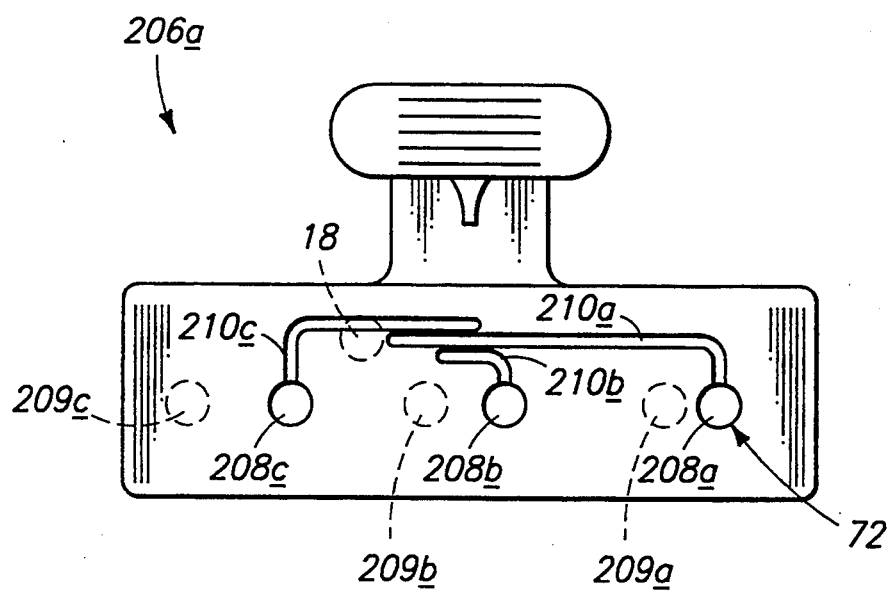
FIG. 13 is an enlarged forward end view of a sliding member as used in the system of FIG. 12.

A single valve member 206a is shown in FIG. 13. It has three individual passageways 208a–208c corresponding to each of the three associated syringes, respectively. Three valve inlet ports 209a–209c, leading from the associated syringes 102a–102c, respectively, are shown by dashed lines in FIG. 13. Valve outlet port 18a is also shown in dashed lines. Individual passageways 208 are positioned at a different spacing or pitch than inlet ports 209, so that each passageway 208 aligns with a corresponding valve inlet port 209 at a different selected position of valve member 206. Passageways 208 are formed as already described, each including an open channel 210 which aligns, at an appropriate position of valve member 206, with valve outlet port 18.

In use, a nurse or other care-giver would actuate slide valve assembly 204 to select a fluid withdrawal syringe. That syringe would then be withdrawn to obtain a blood return. The slide valve assembly would then be actuated to select a saline syringe, and that syringe would be depressed to inject saline. Finally, the slide valve assembly would be actuated to select an anticoagulant syringe, and heparin would be injected into the catheter's lumen.

The embodiment shown by FIG. 12 has another feature which is useful in some situations to obtain blood samples through a catheter lumen. It is often desired to obtain a blood sample, for analysis, immediately upon inserting a CVC. To obtain such a sample without requiring additional procedures and equipment, one of the fluid withdrawal syringes has a discharge port 220 at its forward end for discharging withdrawn blood into an external collection device. Discharge port 220 preferably comprises a Luer-lok connector, mounted for fluid communication with fluid withdrawal syringe 102a. During normal operation, port 220 is sealed with a mating cap 222. However, once blood is withdrawn into the fluid withdrawal syringe, the cap can be removed and a blood collection container can be connected thereto. The plunger of the fluid withdrawal syringe can then be depressed to discharge the withdrawn blood into the blood container. Other types of connectors, rather than Luer-lok connectors, could advantageously be used. For instance, a needle-less coupling such as used with typical vacuum blood collection containers could be substituted for the Luer-lok connector shown in FIG. 12.

It should be noted that while the preferred embodiments of the invention are particularly advantageous when initially installing a multi-lumen CVC, they will also find application during routine CVC maintenance. For instance, it is usually necessary to inject additional amounts of heparin into CVC lumens at period intervals. This is typically done at least once during every eight hour shift. The embodiments described above can be used to perform such CVC maintenance and will thereby eliminate the need to gather multiple needle-type syringes for carrying out this task.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A central venous catheter initialization and access system for initializing and accessing a venous catheter having multiple lumens, the system comprising:

a support base having a plurality of integrally-mounted syringes, the syringes being organized as discrete groups corresponding to individual lumens of a multi-lumen central venous catheter, each descrete syringe group being spaced from the other distinct syringe groups, each discrete group comprising at least a flush syringe and an anti-coagulant syringe;

the support base having an integrally-mounted multi-position valve assembly;

the multi-position valve assembly having a plurality of individual valve inlet ports in fluid communication with the respective individual syringes;

the multi-position valve assembly having a separate valve outlet port for each discrete group of syringes;

a plurality of mating connectors in fluid communication with the valve outlet ports for simultaneous connection of the valve outlet ports to individual lumens of a multi-lumen central venous catheter; and the valve assembly being manually actuable to selectively connect between one syringe of each discrete group and that group's corresponding valve outlet port to facilitate sequential injection from the flush and anti-coagulant syringes into individual lumens of a multi-lumen central venous catheter.

2. A central venous catheter initialization and access system as recited in claim 1, the valve assembly having a separate movable valve member associated with each discrete group of syringes, each valve member being manually movable between a flush position which connects the flush syringe of the associated syringe group to its respective outlet port, and an anti-coagulant position which connects the anti-coagulant syringe of the associated syringe group to its respective outlet port.

3. A central venous catheter initialization and access system for initializing and accessing a venous catheter having multiple lumens, the system comprising:

a support base having a plurality of integrally-mounted syringes, the syringes being organized as discrete groups corresponding to individual lumens of a multi-lumen central venous catheter, each discrete group comprising at least a flush syringe and an anti-coagulant syringe;

the support base having an integrally-mounted multi-position valve assembly;

the multi-position valve assembly having a plurality of individual valve inlet ports in fluid communication with the respective individual syringes;

the multi-position valve assembly having a separate valve outlet port for each discrete group of syringes;

a plurality of mating connectors in fluid communication with the valve outlet ports for simultaneous connection of the valve outlet ports to individual lumens of a multi-lumen central venous catheter; and the valve assembly being manually actuable to selectively connect between one syringe of each discrete group and that group's corresponding valve outlet port to facilitate sequential injection from the, flush and anti-coagulant syringes into individual lumens of a multi-lumen central venous catheter;

the discrete syringe groups including fluid withdrawal syringes, at least one of the fluid withdrawal syringes including a discharge port for discharging withdrawn fluid into an external collection container.

4. A central venous catheter initialization and access system for initializing and accessing a venous catheter having multiple lumens, the system comprising:

a support base having a plurality of integrally-mounted syringes, the syringes being organized as discrete groups corresponding to individual lumens of a multi-lumen central venous catheter each discrete group comprising at least a flush syringe and an anti-coagulant syringe;

the support base having an integrally-mounted multi-position valve assembly;

the multi-position valve assembly having a plurality of individual valve inlet ports in fluid communication with the respective individual syringes;

the multi-position valve assembly having a separate valve outlet port for each discrete group of syringes;

a plurality of mating connectors in fluid communication with the valve outlet ports for simultaneous connection of the valve outlet ports to individual lumens of a multi-lumen central venous catheter; and the valve assembly being manually actuable to selectively connect between one syringe of each discrete group and that group's corresponding valve outlet port to facilitate sequential injection from the flush and anti-coagulant syringes into individual lumens of a multi-lumen central venous catheter, the valve assembly having a single movable valve member which is manually movable to selectively connect between one syringe of each discrete group and that group's corresponding valve outlet port.

5. A central venous catheter initialization and access system for initializing and accessing a venous catheter having multiple lumens, the system comprising:

a support base having a plurality of integrally-mounted syringes, the syringes being organized as discrete groups corresponding to individual lumens of a multi-lumen central venous catheter each discrete group comprising at least a flush syringe and an anti-coagulant syringe;

the support base having an integrally-mounted multi-position valve assembly;

the multi-position valve assembly having a plurality of individual valve inlet ports in fluid communication with the respective individual syringes;

the multi-position valve assembly having a separate valve outlet port for each discrete group of syringes;

a plurality of mating connectors in fluid communication with the valve outlet ports for simultaneous connection of the valve outlet ports to individual lumens of a multi-lumen central venous catheter; and the valve assembly being manually actuable to selectively connect between one syringe of each discrete group and that group's corresponding valve outlet port to facilitate sequential injection from the flush and anti-coagulant syringes into individual lumens of a multi-lumen central venous catheter, the valve assembly having a single movable valve member which is manually movable between a flush position which simultaneously connects all the flush syringes to their respective outlet ports, and an anti-coagulant position which simultaneously connects all the anti-coagulant syringes to their respective outlet ports.

6. A central venous catheter initialization and access system for initializing and accessing a venous catheter having multiple lumens, the system comprising:

support base having a plurality of integrally-mounted syringes, the syringes being organized as discrete groups corresponding to individual lumens of a multi-lumen central venous catheter, each discrete group comprising at least a flush syringe and an anti-coagulant syringe;

the support base having an integrally-mounted multi-position valve assembly;

the multi-position valve assembly having a plurality of individual valve inlet ports in fluid communication with the respective individual syringes;

the multi-position valve assembly having a separate valve outlet port for each discrete group of syringes;

a plurality of mating connectors in fluid communication with the valve outlet ports for simultaneous connection of the valve outlet ports to individual lumens of a multi-lumen central venous catheter; and the valve assembly being manually actuable to selectively connect between one syringe of each discrete group and that group's corresponding valve outlet port to facilitate sequential injection from the flush and anti-coagulant syringes into individual lumens of a multi-lumen central venous catheter, the valve assembly having at least one movable valve member which is movable to a vent position to connect a plurality of the valve inlet ports to ambient atmosphere to allow expulsion of air from a plurality of the syringes.

7. A central venous catheter initialization and access system for initializing and accessing a central venous catheter having multiple lumens, the system comprising:

a generally planar underlying support sheet;

a plurality of syringes mounted atop the support sheet in discrete spaced groups corresponding to individual lumens of a multi-lumen central venous catheter, each discrete syringe group comprising at least a flush syringe and an anti-coagulant syringe;

a multi-position valve assembly mounted atop the support sheet;

the multi-position valve assembly having a plurality of individual valve inlet ports in fluid communication with the respective individual syringes;

the multi-position valve assembly having a separate valve outlet port for each discrete syringe group;

a plurality of mating connectors in fluid communication with the valve outlet ports simultaneous connection of the valve outlet ports to individual lumens of a multi-lumen central venous catheter;

the underlying support sheet extending beneath the mating connectors to provide a sterile field beneath the mating connectors; and the valve assembly having at least one valve member which is movable to select between the flush syringes and the anti-coagulant syringes and to provide fluid communication between the selected syringes and their corresponding outlet ports for facilitating sequential injection from the flush and anti-coagulant syringes into individual lumens of a multi-lumen central venous catheter.

8. A central venous catheter initialization and access system for initializing and accessing a central venous catheter having multiple lumens, the system comprising:

a generally planar underlying support sheet;

a plurality of syringes mounted atop the support sheet in discrete spaced groups corresponding to individual lumens of a multi-lumen central venous catheter, each discrete syringe group comprising at least a flush syringe and an anti-coagulant syringe;

a multi-position valve assembly mounted atop the support sheet;

the multi-position valve assembly having a plurality of individual valve inlet ports in fluid communication with the respective individual syringe;

the multi-position valve assembly having a separate valve outlet port for each discrete syringe group;

a plurality of mating connectors in fluid communication with the valve outlet ports for simultaneous connection of the valve outlet ports to individual lumens of a multi-lumen central venous catheter;

the underlying support sheet extending beneath the mating connectors to provide a sterile field beneath the mating connectors;

the valve assembly having at least one valve member which is movable to select between the flush syringes and the anti-coagulant syringes and to provide fluid communication between the selected syringes and their corresponding outlet ports for facilitating sequential injection from the flush and anti-coagulant syringes into individual lumens of a multi-lumen central venous catheter; and the discrete syringe groups including fluid withdrawal syringes, at least one of the fluid withdrawal syringes including a discharge port for discharging withdrawn fluid into an external collection container.

9. A central venous catheter initialization and access system for initializing and accessing a central venous catheter having multiple lumens, the system comprising:

a generally planar underlying support sheet;

a plurality of syringes mounted atop the support sheet in discrete spaced groups corresponding to individual lumens of a multi-lumen central venous catheter, each discrete syringe group comprising at least a flush syringe and an anti-coagulant syringe;

a multi-position valve assembly mounted atop the support sheet;

the multi-position valve assembly having a plurality of individual valve inlet ports in fluid communication with the respective individual syringes;

the multi-position valve assembly having a separate valve outlet port for each discrete syringe group;

a plurality of mating connectors in fluid communication with the valve outlet ports for simultaneous connection of the valve outlet ports to individual lumens of a multi-lumen central venous catheter;

the underlying support sheet extending beneath the mating connectors to provide a sterile field beneath the mating connectors;

the valve assembly having at least one valve member which is movable to select between the flush syringes and the anti-coagulant syringes and to provide fluid communication between the selected syringes and their corresponding outlet ports for facilitating sequential injection from the flush and anti-coagulant syringes into individual lumens of a multi-lumen central venous catheter, the valve assembly having only a single one of the valve members, said valve member being manually movable between a flush position which simultaneously connects all the flush syringes to their respective outlet ports, and an anti-coagulant position which simultaneously connects all the anti-coagulant syringes to their respective outlet ports.

10. A central venous catheter initialization and access system for initializing and accessing a central venous catheter having multiple lumens, the system comprising:

a generally planar underlying support sheet;

a plurality of syringes mounted atop the support sheet in discrete spaced groups corresponding to individual lumens of a multi-lumen central venous catheter, each discrete syringe group comprising at least a flush syringe and an anti-coagulant syringe;

multi-position valve assembly mounted atop the support sheet;

the multi-position valve assembly having a plurality of individual valve inlet ports in fluid communication with the respective individual syringes;

the multi-position valve assembly having a separate valve outlet port for each discrete syringe group;

a plurality of mating connectors in fluid communication with the valve outlet ports for simultaneous connection of the valve outlet ports to individual lumens of a multi-lumen central venous catheter;

the underlying support sheet extending beneath the mating connectors to provide a sterile field beneath the mating connectors;

the valve assembly having at least one valve member which is movable to select between the flush syringes and the anti-coagulant syringes and to provide fluid communication between the selected syringes and their corresponding outlet ports for facilitating sequential injection from the flush and anti-coagulant syringes into individual lumens of a multi-lumen central venous catheter, the at least one valve member being movable to a vent position to connect a plurality of the valve inlet ports to ambient atmosphere to allow expulsion of air from a plurality of the syringes.

* * * * *